United States Patent
Crespo

(10) Patent No.: US 9,549,854 B1
(45) Date of Patent: Jan. 24, 2017

(54) SAFETY CLEANING TIP

(71) Applicant: Jorge Crespo, Valley Stream, NY (US)

(72) Inventor: Jorge Crespo, Valley Stream, NY (US)

(*) Notice: Subject to any disclaimer, the term of this patent is extended or adjusted under 35 U.S.C. 154(b) by 434 days.

(21) Appl. No.: 14/289,276

(22) Filed: May 28, 2014

Related U.S. Application Data

(60) Provisional application No. 61/828,235, filed on May 29, 2013.

(51) Int. Cl.
*A61F 11/00* (2006.01)

(52) U.S. Cl.
CPC .................. *A61F 11/006* (2013.01)

(58) Field of Classification Search
CPC ....... A61F 11/006; A61F 11/002; A61F 11/00; A61F 11/004; A61F 13/38; A61M 2210/0662; A61M 2210/0668; A61M 2210/0675; A61B 2017/246
USPC ........................................ 606/162, 160, 159
See application file for complete search history.

(56) References Cited

U.S. PATENT DOCUMENTS

| | | | | |
|---|---|---|---|---|
| 651,395 A * | 6/1900 | Stapp | ............. | A61B 17/320708 606/160 |
| 4,329,990 A * | 5/1982 | Sneider | ............. | A61F 13/38 401/196 |
| 4,890,611 A * | 1/1990 | Monfort | ............. | A61B 17/221 600/587 |
| 5,509,921 A * | 4/1996 | Karell | ............. | A61B 1/227 606/162 |
| 5,632,756 A * | 5/1997 | Kruglick | ............. | A61F 11/006 606/160 |
| 5,715,850 A * | 2/1998 | Markgraaf | ............. | A61F 11/006 132/333 |
| D405,570 S | 2/1999 | Broecking | | |
| 5,888,199 A * | 3/1999 | Karell | ............. | A61F 11/006 606/162 |
| 6,026,541 A | 2/2000 | Bailey et al. | | |
| 6,033,417 A * | 3/2000 | Tseng | ............. | A61F 11/006 606/106 |
| 6,059,803 A | 5/2000 | Spilman | | |
| 6,187,021 B1 | 2/2001 | Wim | | |
| 6,406,484 B1 | 6/2002 | Lang | | |
| D494,672 S | 8/2004 | Wang | | |
| 6,939,360 B2 * | 9/2005 | Crespo | ............. | A61F 11/006 606/162 |
| 6,991,638 B2 | 1/2006 | Wang | | |
| D594,968 S | 6/2009 | Sebban | | |
| 7,951,106 B1 * | 5/2011 | Perez | ............. | A61F 11/006 604/11 |
| 8,777,972 B2 * | 7/2014 | Burres | ............. | A61F 11/006 606/162 |

(Continued)

*Primary Examiner* — Katrina Stransky
(74) *Attorney, Agent, or Firm* — Goldstein Law Offices, P.C.

(57) ABSTRACT

A device operative having a rotating cleaning tip for cleaning a narrow channel, such as an ear canal. In one embodiment, the tip is coupled to a handle with a motor that rotates the tip. The rotating tip has a plurality of strips that bow outwardly, scraping debris from the walls without debris accumulating and impacting along a channel wall. The bowing strips provide entry slits to capture debris into the tip, the strips closing after capture, removing debris when the tip withdraws from the channel. The device has a safety ring disposed around the tip, the safety ring operative for limiting penetration into a narrow canal when cleaning.

12 Claims, 11 Drawing Sheets

(56) References Cited

U.S. PATENT DOCUMENTS

| | | | |
|---|---|---|---|
| 8,784,421 B2* | 7/2014 | Carrison | A61B 17/1604 606/113 |
| 2003/0135228 A1* | 7/2003 | Crespo | A61F 11/006 606/162 |
| 2004/0034379 A1* | 2/2004 | Crespo | A61F 11/006 606/162 |
| 2006/0276816 A1* | 12/2006 | Eckman | A61B 17/320708 606/160 |
| 2008/0142385 A1* | 6/2008 | Stein | A61F 13/38 206/362 |
| 2010/0312198 A1* | 12/2010 | Guidi | A61M 35/006 604/257 |
| 2011/0066172 A1 | 3/2011 | Silverstein | |
| 2012/0296355 A1* | 11/2012 | Burres | A61F 11/006 606/162 |

* cited by examiner

SAFETY CLEANING TIP

CROSS-REFERENCE TO RELATED APPLICATIONS

This application is a nonprovisional utility application of the provisional patent application, Ser. No. 61/828,235 filed in the United States Patent Office on May 29, 2013 and claims the priority thereof and is expressly incorporated herein by reference in its entirety.

TECHNICAL FIELD

The present disclosure relates generally to a cleaning tool. More particularly, the present disclosure relates to a safety cleaning device with a rotating tip for removing debris in a narrow channel.

BACKGROUND

Cleaning narrow channels is difficult. Whether it is an ear canal, a channel in an engine, or a narrow duct in a machine, removing debris when cleaning is a problem.

Most cleaning tools push debris against the sides of the channel or canal, allowing the debris to build up. If the canal has a narrow strait, debris accumulates at the narrow point.

Most otolaryngologists recommend that people do not attempt to remove wax and debris from the ear canal because the wax and debris becomes impacted in the canal. People continue to insert cotton-tip swabs into their ear canals despite the warnings, causing wax impaction and temporary hearing loss. Others have developed vacuum systems to remove debris, however, the vacuum can harm the ear drum.

While these units may be suitable for general use, they would not be as suitable for the purposes of the present disclosure as disclosed hereafter.

In the present disclosure, where a document, act or item of knowledge is referred to or discussed, this reference or discussion is not an admission that the document, act or item of knowledge or any combination thereof was at the priority date, publicly available, known to the public, part of common general knowledge or otherwise constitutes prior art under the applicable statutory provisions; or is known to be relevant to an attempt to solve any problem with which the present disclosure is concerned.

While certain aspects of conventional technologies have been discussed to facilitate the present disclosure, no technical aspects are disclaimed and it is contemplated that the claims may encompass one or more of the conventional technical aspects discussed herein.

BRIEF SUMMARY

An aspect of an example embodiment in the present disclosure is to provide a device for cleaning a narrow channel that rotates when inserted into the channel. Accordingly, the present disclosure provides a device having a rotating cleaning tip coupled to a handle with a motor that rotates the tip.

Another aspect of an example embodiment in the present disclosure is to provide a device for cleaning a narrow channel without accumulating along a canal wall. Accordingly, an aspect of an example embodiment in the present disclosure provides a rotating tip with a plurality of strips that bow outwardly, scraping debris from the walls.

A further aspect of an example embodiment in the present disclosure is to provide a device for cleaning a narrow channel that removes debris when cleaning. Accordingly, an aspect of an example embodiment in the present disclosure provides a tip that has a plurality of bowing strips that provide entry slits to capture debris into the tip, the strips closing after capture, removing debris when the tip withdraws from the channel.

Yet another aspect of an example embodiment in the present disclosure is to provide a device for cleaning a narrow channel with a limit to penetration. Accordingly, an aspect of an example embodiment in the present disclosure provides a device having a safety ring disposed around a tip, the safety ring operative for limiting penetration into a narrow channel when cleaning.

The present disclosure describes a device operative for cleaning a narrow channel, such as an ear canal, the device having a rotating cleaning tip. In one embodiment, the tip is coupled to a handle with a motor that rotates the tip. The rotating tip has a plurality of strips that bow outwardly, scouring debris from the walls without accumulating and impacting along a canal wall. The bowing strips provide entry slits to capture debris into the tip, the strips closing after capture, removing debris when the tip withdraws from the canal. The device has a safety ring disposed around the tip, the safety ring operative for limiting penetration into the narrow canal when cleaning.

The present disclosure addresses at least one of the foregoing disadvantages. However, it is contemplated that the present disclosure may prove useful in addressing other problems and deficiencies in a number of technical areas. Therefore, the claims should not necessarily be construed as limited to addressing any of the particular problems or deficiencies discussed hereinabove. To the accomplishment of the above, this disclosure may be embodied in the form illustrated in the accompanying drawings. Attention is called to the fact, however, that the drawings are illustrative only. Variations are contemplated as being part of the disclosure.

BRIEF DESCRIPTION OF THE DRAWINGS

In the drawings, like elements are depicted by like reference numerals. The drawings are briefly described as follows.

The present disclosure now will be described more fully hereinafter with reference to the accompanying drawings, which show various example embodiments. However, the present disclosure may be embodied in many different forms and should not be construed as limited to the example embodiments set forth herein. Rather, these example embodiments are provided so that the present disclosure is thorough, complete and fully conveys the scope of the present disclosure to those skilled in the art.

DETAILED DESCRIPTION OF THE PREFERRED EMBODIMENTS

Figure 9A:
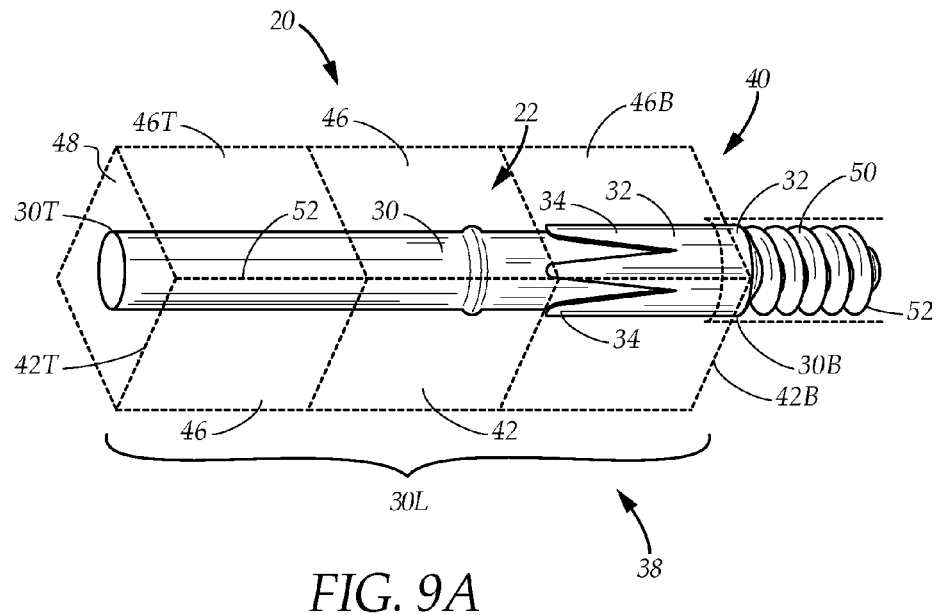
FIG. 9A is a perspective view of an example embodiment of the tip showing a plurality of outer panels in outline, and an inner stem.

FIG. 9A illustrates a tip 20 for a safety cleaning device operative for cleaning debris from a narrow channel, such as an ear canal. The tip 20 rotates when cleaning the canal. The tip can be free standing, rotated by hand in one embodiment or coupled to a handle that houses a motor operative for rotating the tip in a further embodiment.

The tip 20 has an inner shaft 30 having a top 30T and a bottom 30B, the bottom 30B having a collar 32, the collar 32 having a plurality of radial prongs 34. The shaft 30 has a length 30L.

The tip 20 has a top member 48 coupled to the top 30T of the inner shaft 30, the tip having a bottom rotatable stem 50 coupled to the inner shaft 30 below the shaft bottom 30B below the collar. The tip has a striped outer head 40, the head having a plurality of strips 42, the strips defining an interior space 22, the strips extending along the length 30L of the shaft 30. Each strip has a top 42T and a bottom 42B, the top 42T of each strip coupled to the top member 48, the bottom 42B coupled to the stem 50 adjacent to and below the collar 32.

In a further embodiment, the strips have a plurality of panels 46, each strip 40 have a top panel 46T hingedly coupled to the top member 48, a bottom panel 46B hingedly coupled to the stem 30, each panel 46 hingedly connecting to an adjacent panel 46 along the length of the stem 30L.

Figure 9B:
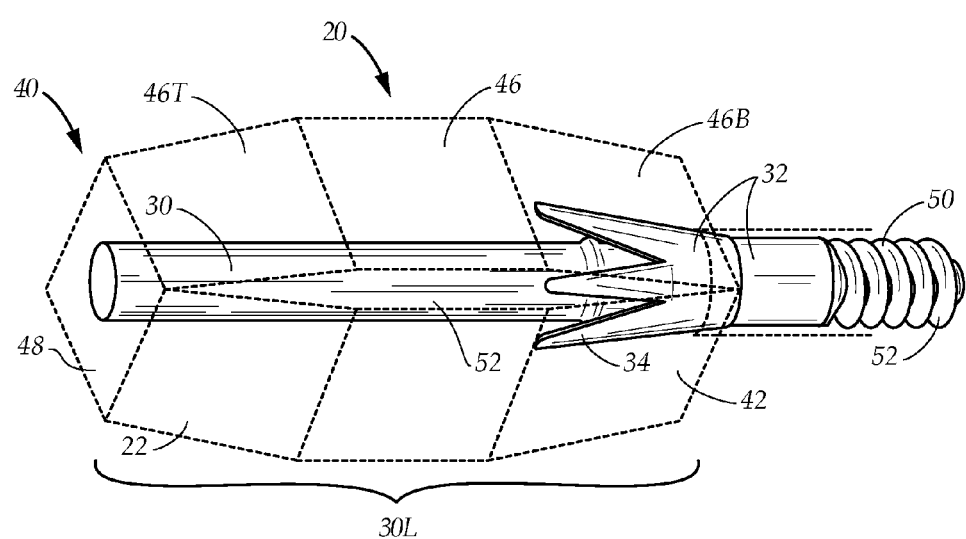
FIG. 9B, similar to FIG. 9A, is a perspective view of an example embodiment of the outer panels of the tip in outline forming a plurality of slits and the inner stem contracting.

FIG. 9B illustrates the tip 20 as it rotates and deforms. The strips 42 of the head 40 rotate when the outer stem 50 rotates, the stem 50 withdrawing the inner shaft 30 through the collar 30 when the stem rotates in a direction, decreasing the length 30L of the shaft 30 inside the head 22, the rotating stem 50 extending the prongs 34 of the collar 32 radially away from the inner shaft 30 as the inner shaft withdraws, pulling the top member 48 towards the collar 32. When the tip 20 rotates, a spring 52 inside the stem 50 rotates the collar 32, extending the prongs 34, pushing the strips 42 of the head away from each other. The prongs 34 of the collar and the decreased inner shaft length 30L push the strips 42 outward away from the shaft, the strips 42 bowing while rotating, the bowing of the strips providing entry slits 52 between the strips 42.

When the strips 42 rotate within a canal having a wall, the strips 42 sweep debris from the canal wall into the entry slits 52 into the interior space 22. The stem 50 extends the inner shaft 30 into the head 40 when the stem rotates in an opposite direction, the shaft 30 extending the strips along the length of the shaft 30L, as shown in FIG. 9A, closing the entry slits 52, capturing the debris for disposal as the tip 20 withdraws from the canal.

In one embodiment, each strip 42 is a unitary piece, constructed from flexible material, causing the strip to bow into an arc shape, outwardly away from the shaft 30.

In a further embodiment, the strips have a plurality of panels 46, each strip 40 have a top panel 46T hingedly coupled to the top element, a bottom panel 46B hingedly coupled to the stem 30, each panel 46 hingedly connecting to an adjacent panel 46 along the length of the stem 30L. The hingedly coupled panels allow the strip to bow into the arc shape, similarly to the flexible unitary strip.

Figure 2:
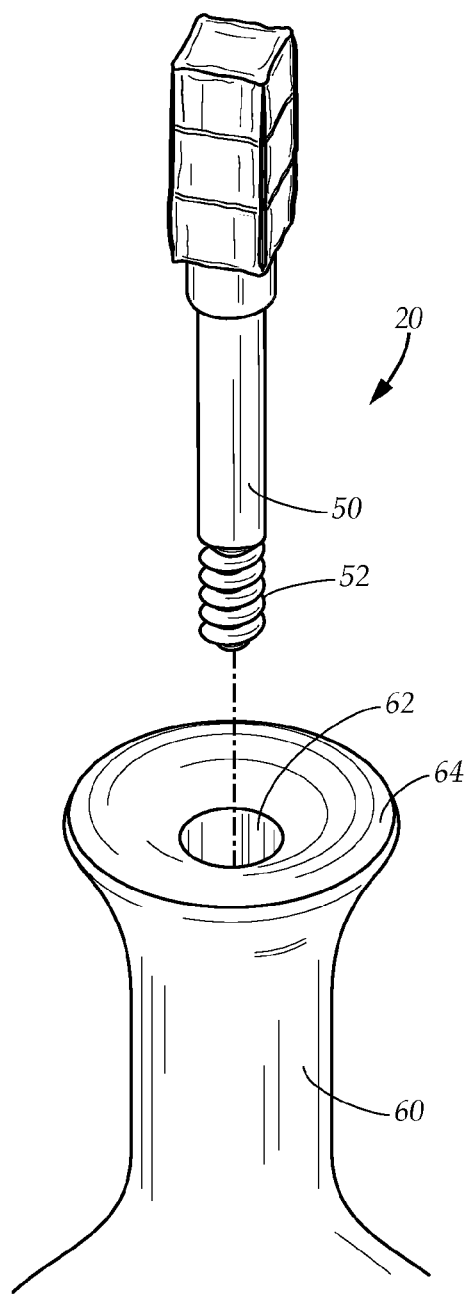
FIG. 2 is a perspective view of an example embodiment of a tip attaching to a handle.

FIG. 2 shows the tip 20 before coupling to a handle 60. The stem is threaded to aid coupling with the handle. The handle has a center bore 62 to receive the stem. The handle 60 has a safety ring 64 around the center bore 62 operative for limiting penetration of the tip 20 into the canal.

Figure 10:
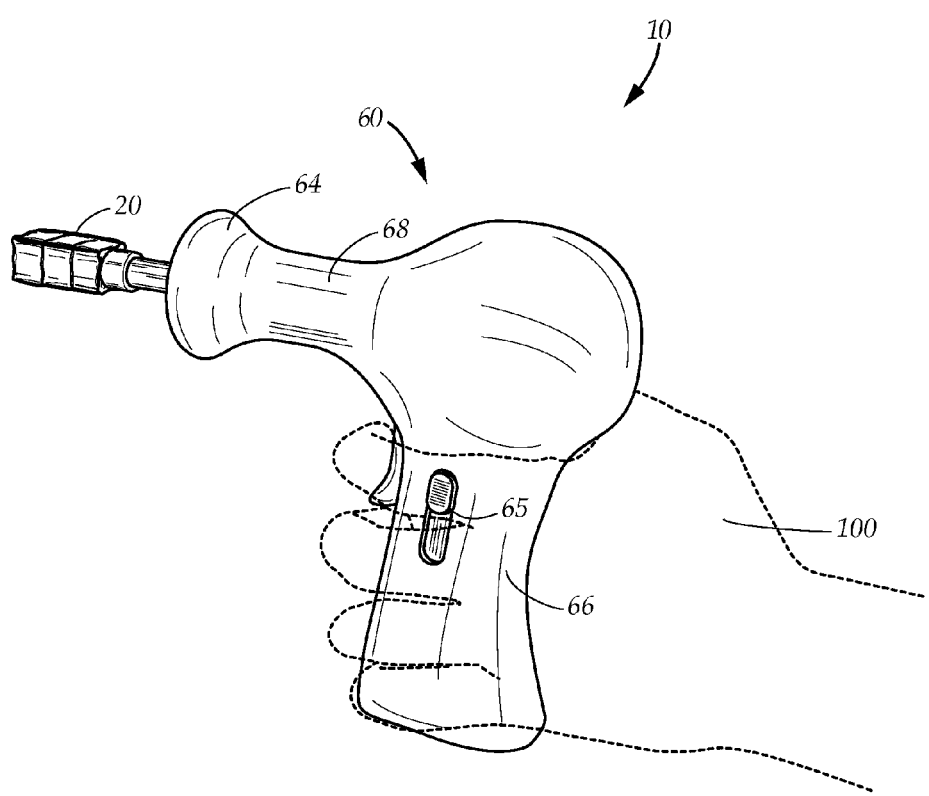
FIG. 10 is a perspective view of an example embodiment of a motorized handle engaging the tip.

FIG. 10 shows the device 10 with the tip 20 coupled to the handle 60. The handle has a grip 66 for holding by a hand 100 and a switch 65 operative for engaging an internal motor. At about a right angle, the handle 60 has a shank 68 having the safety ring 64 with the bore, which is not visible in this drawing.

Figure 3:
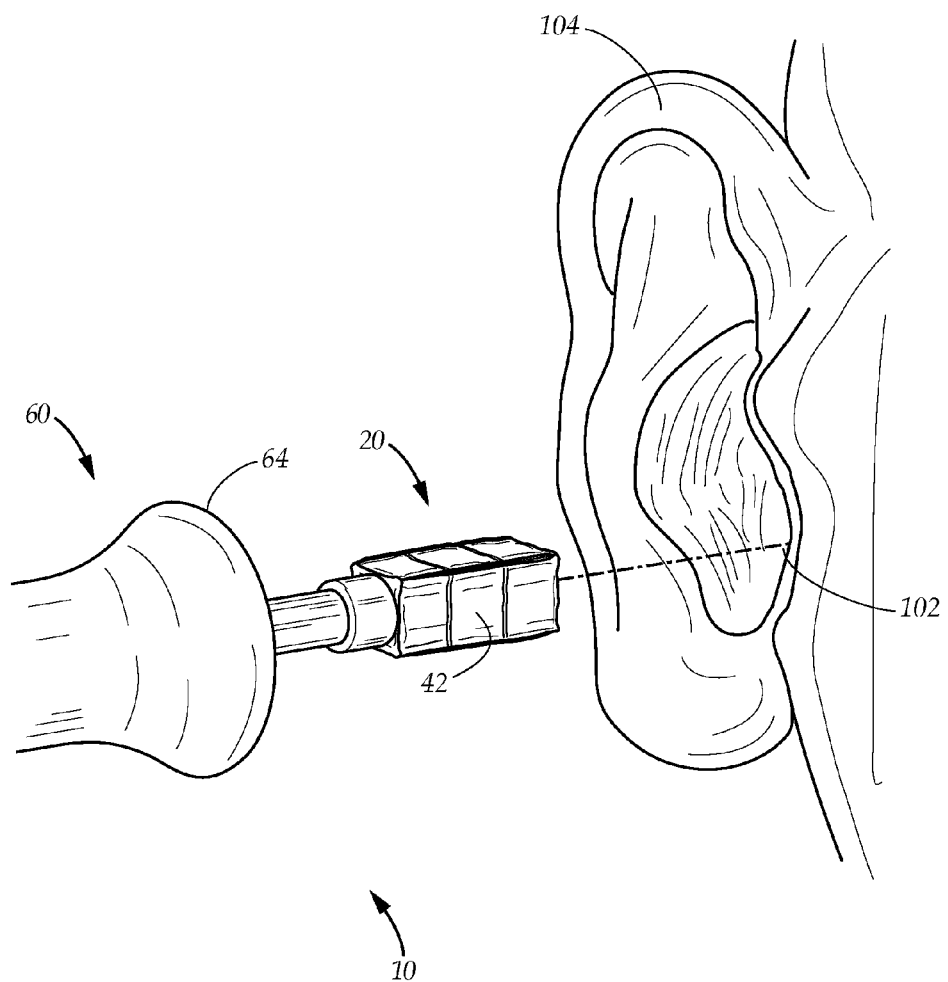
FIG. 3 is a perspective view of an example embodiment of the tip entering an ear canal.

FIG. 3 shows the device 10 in use. In the non-limiting illustration, the device is operative for cleaning debris from an ear canal 102. It is understood that the device is operative for cleaning debris from many kinds of narrow channels, such as, but not limited to, an ear canal, an engine channel, or a machine duct as non-limiting examples.

In the drawing, the tip 10 is in a closed position, with the strips closely adjacent, absent any open entry slits. The tip 20 is about to enter the ear canal 102 through the ear pinna 104, the pinna and ear canal parts of a human outer ear.

Figure 4:
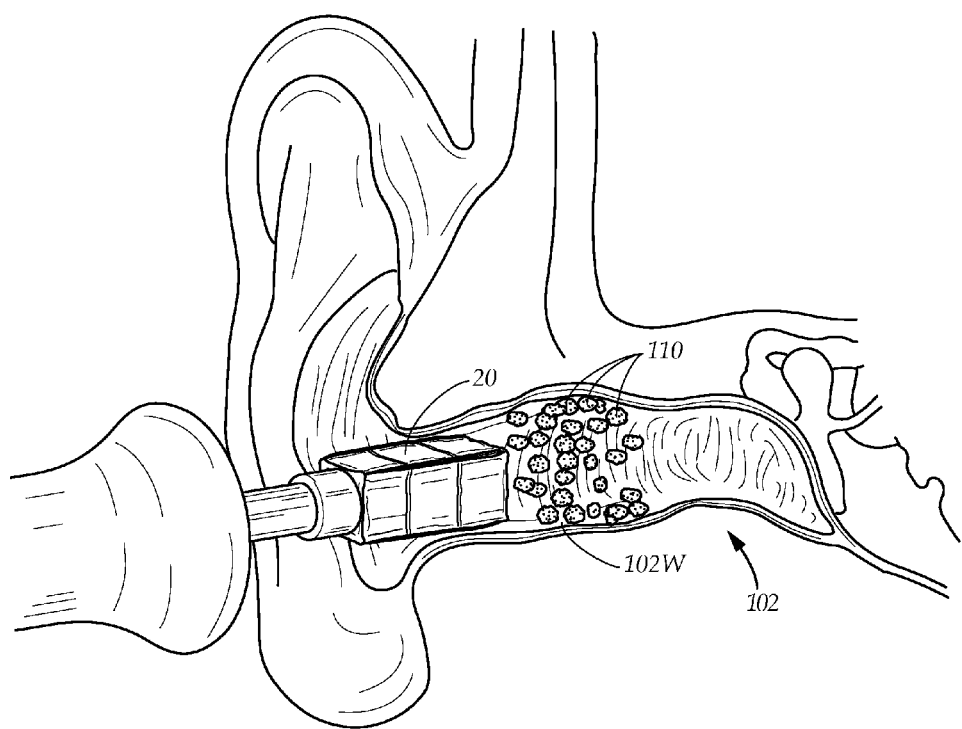
FIG. 4 is a perspective view of an example embodiment of the unopened tip in the ear canal having debris and a plurality of wax particles.

FIG. 4 shows the tip 20 inserting into the canal 102 having debris such as particles 110 of ear wax or cerumen. The canal has a wall 102W.

Figure 5:
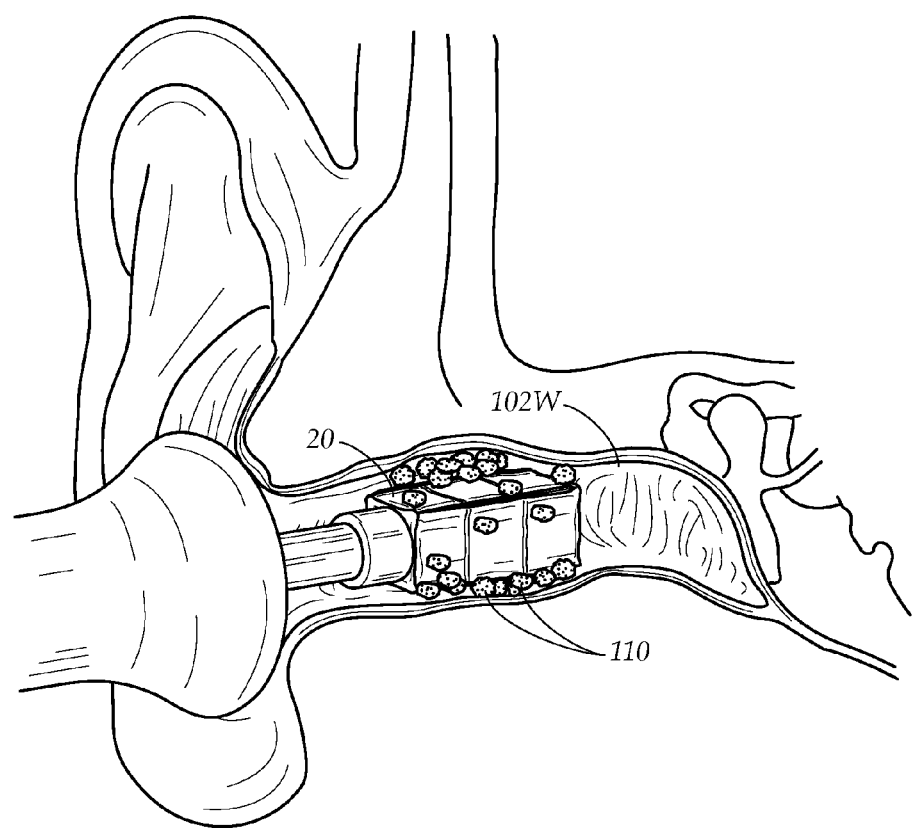
FIG. 5 is a perspective view of an example embodiment of the tip opening in the ear canal.

FIG. 5 shows the particles 110 gathering between the tip 20 and ear canal wall 102W as the tip begins to rotate, scraping the walls.

Figure 6:
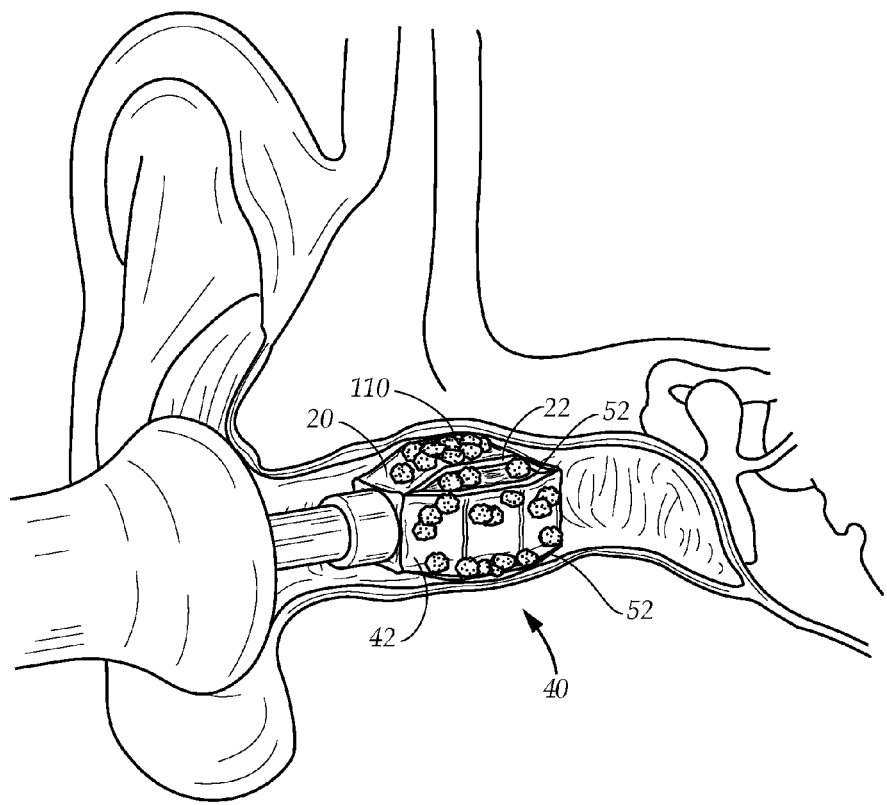
FIG. 6 is a perspective view of an example embodiment of the open tip collecting debris and wax particles.

FIG. 6 demonstrates how the strips begin to bow during rotation, opening the entry slits 52. Debris particles 110 enter the interior space 22 as the tip 20 rotates. Particles 110 are engaged by the head 40 and not impacted onto the canal wall 102W.

Figure 7:
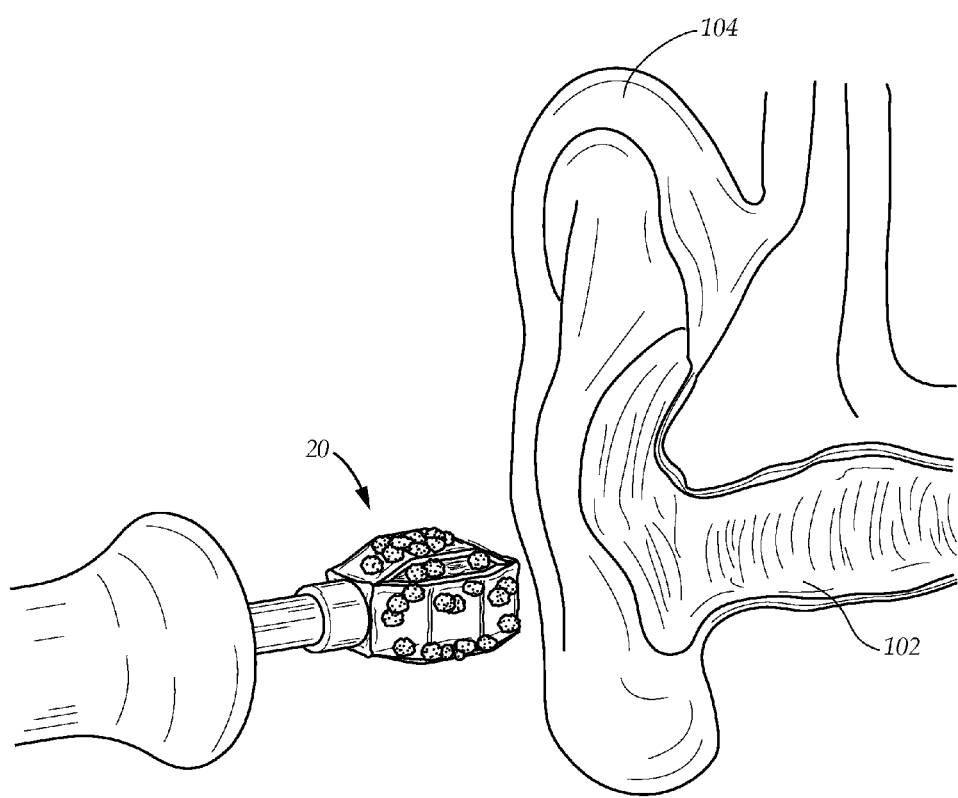
FIG. 7 is a perspective view of an example embodiment of the tip removing from the ear canal, bearing the collected debris and wax particles.

FIG. 7 shows the tip 20 containing the particles 110 removing from the ear canal 102 and pinna 104, without impacting the debris particles onto the canal wall. In another embodiment, the tip is rotated in an opposite direction, closing the entry slits, capturing the debris inside before withdrawing from the ear canal 102.

Figure 8:
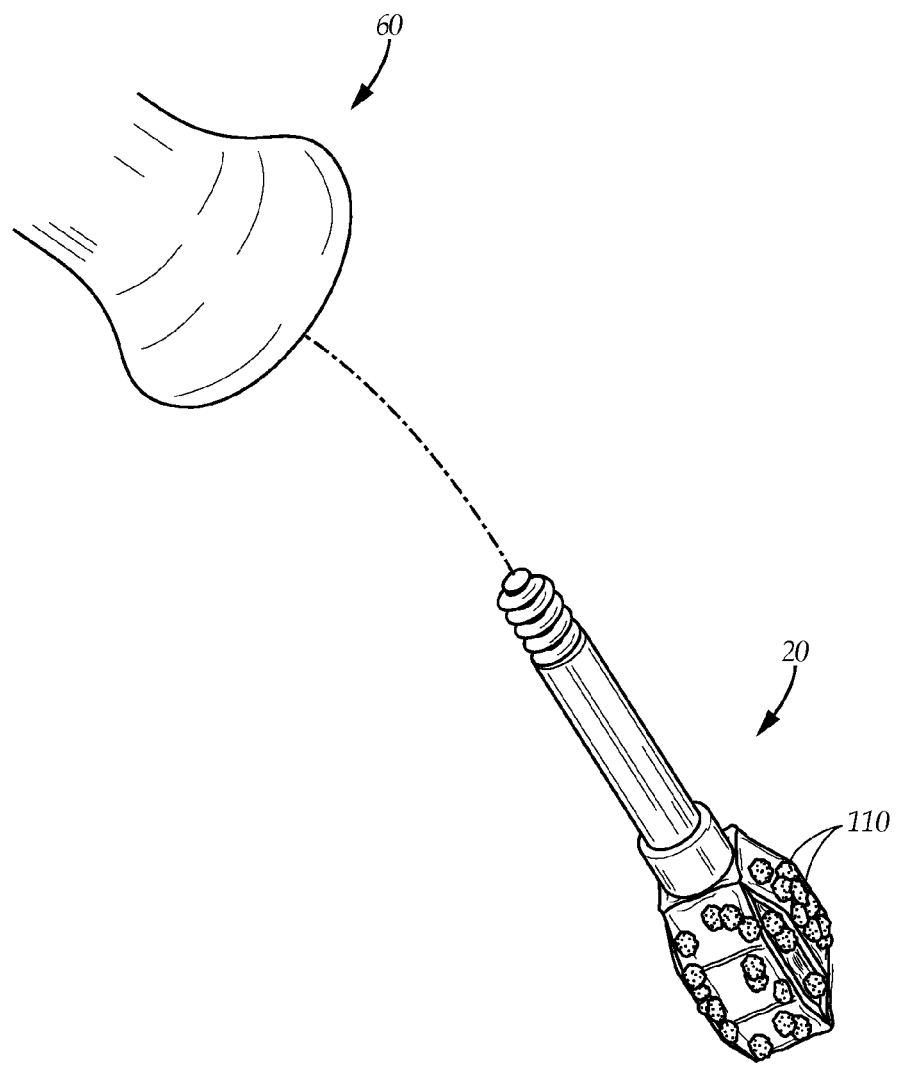
FIG. 8 is a perspective view of an example embodiment of the handle ejecting the tip together with the collected debris and wax particles.

FIG. 8 shows the handle 60 ejecting the tip 20 with debris particles 110 from the bore. In one embodiment, the tips are disposable.

Figure 1:
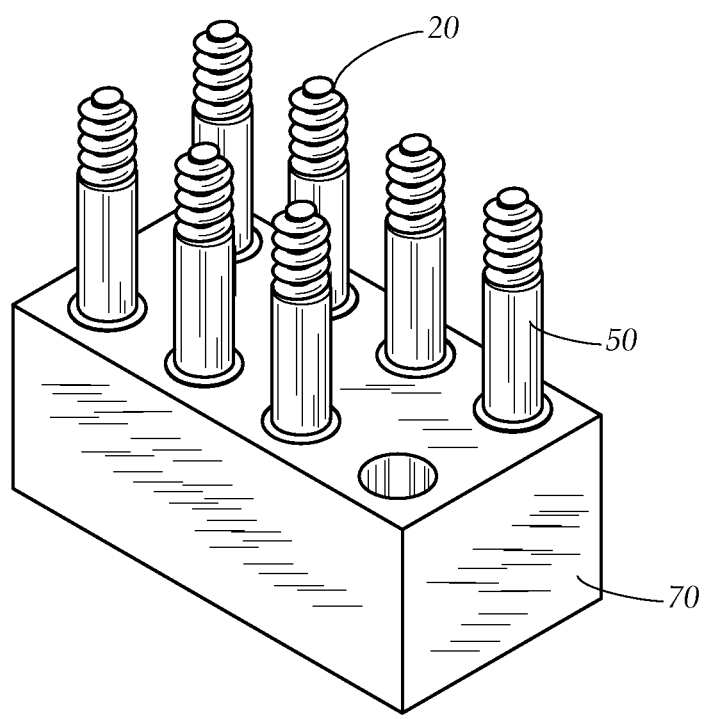
FIG. 1 is a perspective view of an example embodiment of an array of tips disposed in a holder, the tips presenting for attaching to a handle.

FIG. 1 shows a plurality of tips 20 arrayed in a rack 70 with the stems 20 upward operative for engaging the bore of the handle. In one embodiment, each tip is color coded for different family members. In a further embodiment, the tips 20 are disposable and are provided in the rack 70 for easy dispensing.

Referring again to FIG. 9A, a tip is produced by providing the inner shaft 30 having the top 30T and the bottom 30B and coupling the collar 32 with radial prongs 34 to the bottom of the shaft. The top member 48 is coupled to the top 30T of the shaft. The stem 50 is coupled to the bottom 30B of the shaft 30 below the collar 32. The head 40 defines the interior space 22 by coupling the strips 42 of the head along the shaft, each strip having the top 42T and the bottom 42B, the top coupled to the top member 48 and the bottom 42B coupled to the stem 50 adjacent to and below the collar 32. The spring 52 is placed below the collar 32 on the stem 50.

In one embodiment, the strips are produced from the plurality of panels 46 hingedly connected.

Figure 11:
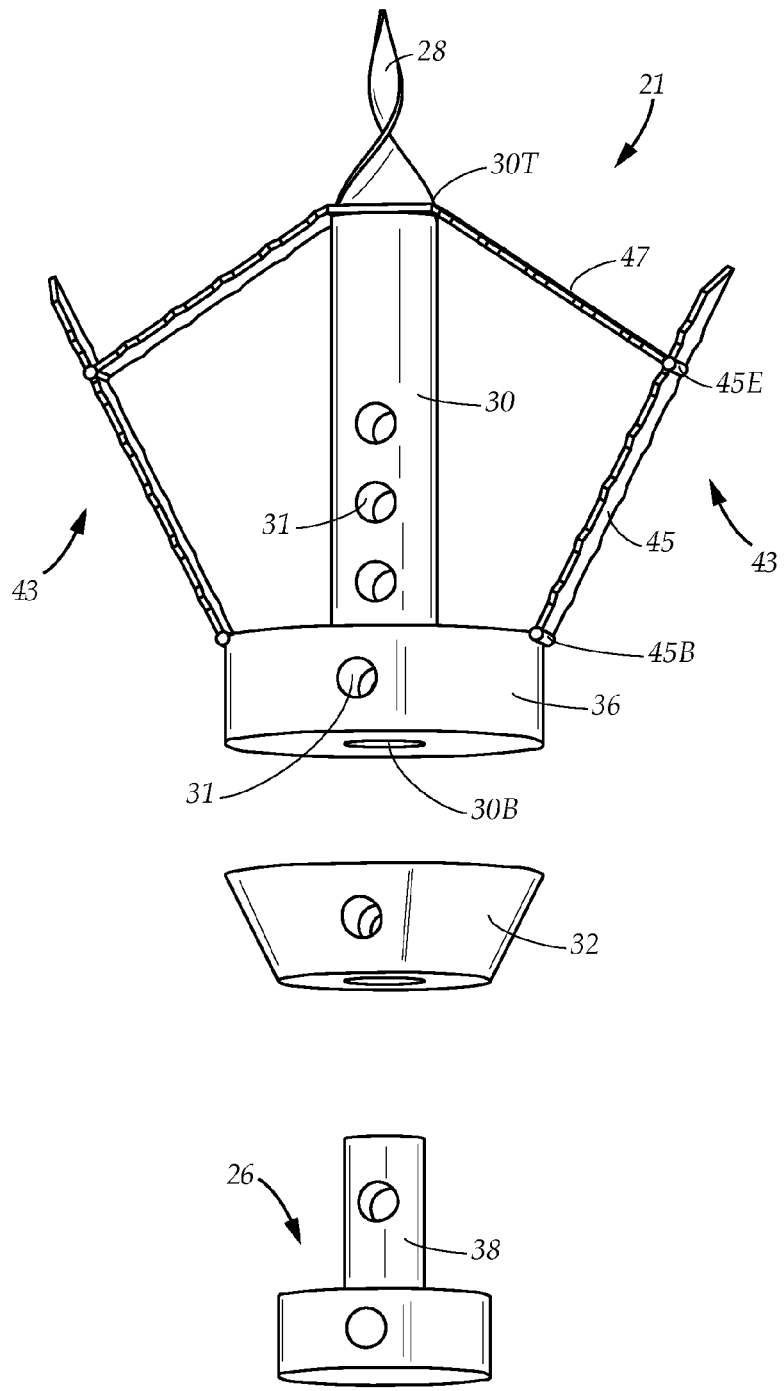
FIG. 11 is an exploded view of another example embodiment of the tip.

Another example embodiment of the tip 21 is illustrated in FIG. 11. The inner shaft 30 has the top 30T and the bottom 30B. The shaft 30 has a plurality of openings 31 configured for receiving a pin.

An expansion ring 36 encircles the shaft 30 towards the bottom 30B of the shaft. The expansion ring 36 is configured for sliding along the inner shaft 30, the ring prevented from sliding along the shaft when the pin inserts into an opening 31 on the shaft 30, the pin blocking the ring 36.

The tip 21 has plurality of strips 43, each strip 43 having a paddle 45 having a first end 45E hingedly connecting to a support 47 and a second end 45B hingedly attaching to the expansion ring 36.

The support 47 has a first end 47T that attaches to the top 30T of the inner shaft 30 and a second end 47E connecting to the paddle 45, the strips 43 bowing outwards as the expansion ring 32 slides toward the top of the inner shaft 30 until encountering the pin, the strips 43 operative for removing debris from the narrow channel as the tip 21 rotates inside a narrow channel.

A spirally shaped blade 28 is at the top 30T of the inner shaft 30.

The collar 32 encircles the expansion ring 36 at the bottom 30B of the inner shaft 30, the collar 32 maintaining the expansion ring 36 on the shaft 30.

An adapter 26 having a rod 38 couples to the inner shaft 30, the rod 38 inserting into the inner shaft 30, the adapter 26 configured for coupling the tip 21 to the handle as illustrated and explained hereinabove.

It is understood that when an element is referred hereinabove as being "on" another element, it can be directly on the other element or intervening elements may be present therebetween. In contrast, when an element is referred to as being "directly on" another element, there are no intervening elements present.

Moreover, any components or materials can be formed from a same, structurally continuous piece or separately fabricated and connected.

It is further understood that, although ordinal terms, such as, "first," "second," "third," are used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

Spatially relative terms, such as "beneath," "below," "lower," "above," "upper" and the like, are used herein for ease of description to describe one element or feature's relationship to another element(s) or feature(s) as illustrated in the figures. It is understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device can be otherwise oriented (rotated 90 degrees or at other orientations) and the spatially relative descriptors used herein interpreted accordingly.

Example embodiments are described herein are schematic illustrations of idealized embodiments. As such, variations from the shapes of the illustrations as a result, for example, of manufacturing techniques and/or tolerances, are to be expected. Thus, example embodiments described herein should not be construed as limited to the particular shapes of regions as illustrated herein, but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

In conclusion, herein is presented a safety cleaning device with a rotating tip. The disclosure is illustrated by example in the drawing figures, and throughout the written description. It should be understood that numerous variations are possible, while adhering to the inventive concept. Such variations are contemplated as being a part of the present disclosure.

What is claimed is:

1. A safety cleaning device for cleaning debris from a narrow channel, comprising:
   a tip having an inner shaft, said inner shaft having a top and a bottom;
   a top member coupled to said inner shaft top;
   a collar, the collar coupled to said inner shaft bottom, the collar having a plurality of radial prongs;
   a rotatable bottom stem coupled to the inner shaft below said collar; and
   a segmented outer head, said head having a plurality of strips, said strips extending along said inner shaft, said strips defining an interior space enclosing said inner shaft, each strip coupled to the top member and to the rotatable bottom stem adjacent to and below the collar, said strips rotating as the bottom stem rotates in one direction, the stem withdrawing the inner shaft through the collar when the stem extends the prongs of said collar, thereby decreasing the length of the shaft inside the head, pulling the top member towards the collar, bowing the strips outward away from the shaft, and providing a plurality of entry slits between the strips operative for collecting debris from a narrow channel.

2. The device as described in claim 1, wherein the strips rotate in an opposite direction, the stem extending the inner shaft and contracting the prongs of said collar, the strips contracting inwardly towards the shaft closing the entry slits thereby trapping the collected debris in the interior space.

3. The device as described in claim 2, wherein said device couples to a handle, the handle having a center bore configured for receiving said stem of said device.

4. The device as described in claim 3, wherein said device is disposable, said device selectively coupling to the handle and selectively detaching from the handle after collecting debris, the debris and device operative for discarding.

5. The device as described in claim 4, wherein the said handle has a safety ring around the center bore, said safety ring configured for limiting penetration of tip into a channel, said device is configured for cleaning an ear canal.

6. The device as described in claim 5, wherein said handle is motorized for rotating said device stem.

7. The device as described in claim 6, wherein the handle having a grip at about a right angle to the center bore.

8. The device as described in claim 1, wherein each strip has a plurality of panels, a top panel hingedly coupled to the top member, a bottom panel hingedly couple to said stem, each panel hingedly connecting to an adjacent panel along the inner stem.

9. The device as described in claim 1, wherein each strip is a unitary piece constructed from flexible material operative for bowing into an arc shape outwardly away from the shaft.

10. A method of cleaning debris from a channel using a safety cleaning tip, comprising:
   inserting a safety cleaning tip into a channel, said tip having an inner shaft, the shaft having a top and a bottom, said bottom coupled to a stem, said shaft encircled by a collar above the stem, said tip having a plurality of strips extending from said stem to the tip top;
   rotating the stem in one direction, the stem withdrawing the inner shaft through the collar, thereby shortening the inner shaft, bowing the strips outwardly outward away from the shaft, providing a plurality of entry slits between the strips;
   collecting debris from the narrow channel by further rotating the stem, the strips scraping the debris from the channel; and
   rotating the stem in an opposite direction, extending the inner shaft, contracting the strips inwardly towards the shaft, operative for extraction from the channel.

11. The method as described in claim 10, wherein the stem is coupled to a handle having a motor, said motor rotating the stem.

12. The method as described in claim 11, wherein said tip is one of a plurality of tips and said tips are arrayed in a rack with the stems facing upward for easily engaging the handle and wherein the step of coupling the stem to the handle includes ejecting a used tip from the handle prior to coupling a new stem to the handle.

* * * * *